United States Patent [19]
Topham

[11] 3,957,051
[45] May 18, 1976

[54] PUMP-TYPE SYRINGE HAVING DOUBLE-ACTING PISTON CONSTRUCTION

[75] Inventor: Silas Charles Topham, Orem, Utah

[73] Assignee: Medical Development Corporation, Salt Lake City, Utah

[22] Filed: Sept. 13, 1974

[21] Appl. No.: 505,786

[52] U.S. Cl. ............................................. 128/278
[51] Int. Cl.² ......................................... A61M 1/00
[58] Field of Search ..................... 128/275–281, 128/218 G, 273; 417/513

[56] References Cited
UNITED STATES PATENTS

| 657,440 | 9/1900 | McCaw | 128/278 |
| 1,444,714 | 2/1923 | Teshima | 128/278 |
| 1,624,990 | 4/1927 | Smith | 417/513 |

Primary Examiner—Lawrence W. Trapp

[57] ABSTRACT

A fluid-transfer syringe for medical usage wherein, by use of such syringe, fluid matter may be removed from an afflicted area, such as a knee, of a patient. The spring-loaded plunger of the subject syringe is provided with a piston constructed to have an automatic fluid bypass during forward strokes. The piston serves thereby as a double-acting piston for both drawing into the area forwardly of the piston the fluid to be expelled and, simultaneously, pumping previously expelled fluid from the syringe barrel to a provided outlet port.

5 Claims, 4 Drawing Figures

PUMP-TYPE SYRINGE HAVING DOUBLE-ACTING PISTON CONSTRUCTION

The present invention relates to fluid-transfer syringes and, more particularly, to a new and improved pumping syringe having a plunger which serves as a double-acting piston to both expel from the syringe previously pumped fluid and, simultaneously, to draw into the syringe barrel additional fluid matter.

As to the prior art, no invention or structure is known wherein, in a pump-type syringe, structure is provided to effect a double-acting piston construction wherein the piston serves both to expel previously drawn fluids and also to pump or suck into the syringe barrel additional fluid for subsequent expulsion.

In the present invention the subject syringe is provided with a plunger, a syringe barrel or cylinder, and the usual cannula needle. Also included are a discharge port and connecting tube proximate a rearmost portion of the syringe barrel. Of importance in the syringe construction is the provision of piston structure, within the plunger design, so that a seal is effected upon plunger withdrawal strokes to thereby provide for an expulsion of previously drawn-out fluids and also to draw in additional fluid from an aflicted area. Return strokes of the plunger, however, are accompanied by an automatic re-adjustment of the piston, of floating design, so that fluid flow is provided through the piston during plunger return strokes. In this manner the fluid previously drawn in by the spring-loaded plunger employed may flow through the piston to be disposed behind the said piston, in a progressive manner, as the plunger is progressively urged forwardly. Thereafter, the piston is designed to seal during a subsequent rearward stroke of the plunger so that the fluid is expelled from the outer port and additional fluid is simultaneously drawn in the syringe barrel.

Accordingly, a principal object of the present invention is to provide a new and improved pump-type syringe for medical use.

An additional object is to provide a syringe having a double-acting piston.

A further object is to provide a pump-type piston which is operative simultaneously to expel previously withdrawn fluid automatically and, additionally, to draw into the cylinder barrel additional fluid from an afflicted patient area.

The features of the present invention which are believed to be novel are set forth with particularity in the appended claims. The present invention, both as to its organization and manner of operation, together with further objects and advantages thereof, may best be understood by reference to the following description, taken in connection with the accompanying drawing in which:

Figure 1:
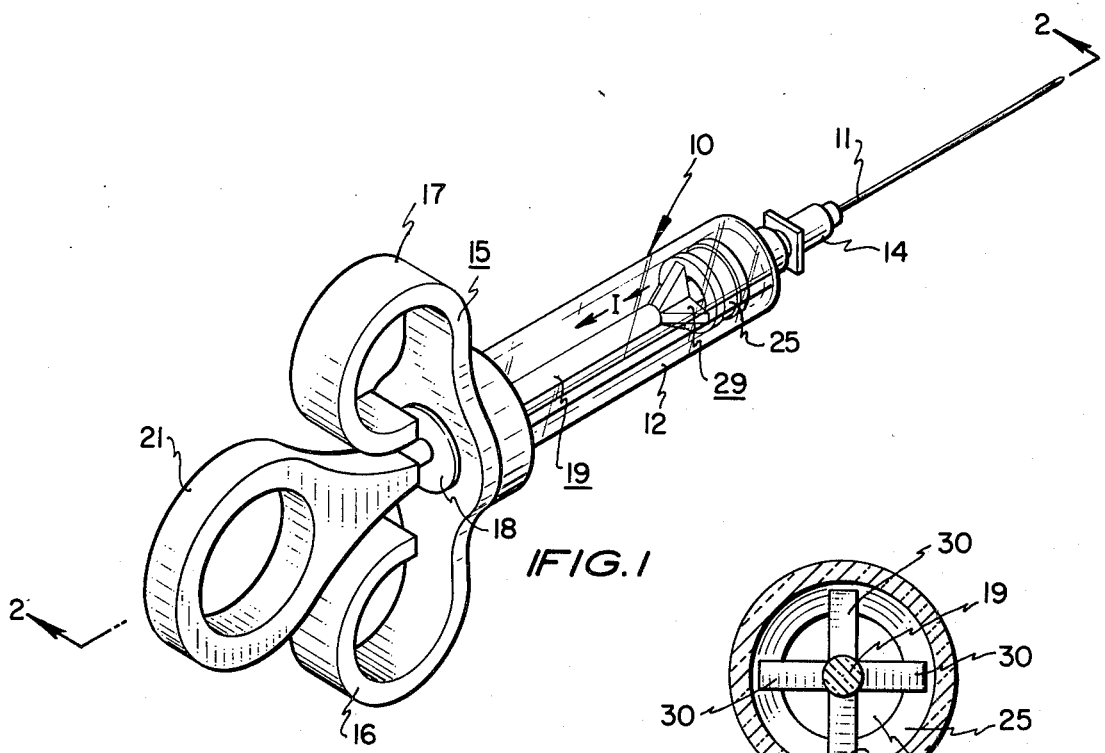
FIG. 1 is a perspective view of a pumping syringe constructed in accordance with the principles of the present invention.

In FIG. 1 the pump-type syringe 10 on the present invention is shown to include a conventional cannula 11 and also a syringe barrel 12. Syringe barrel 12 includes, of course, the forward central hollow boss 13 which receives the cup mount 14 of the cannula 11. See also FIG. 3.

To the rear of the barrel 12 is secured a finger-receiving member 15 configured as shown in the form of a finger grip including arcuate finger-receiving portions 16 and 17. A journaling base or gland 18 may be made of a medium durometer rubber and provided not only a closure for barrel 12 but also a sealing slide receptacle for plunger 19.

As to the latter, the same includes a shank 20 to which a thumb depression end in the form of thumb ring member 21 is secured as by cement or with the employment of any other suitable means. The shaft portion 22 of the plunger thus may have an end 23 that is cemented into a receptacle 24 of member 21.

Piston 25 cooperatively and sealingly engages the inner wall 26 of the barrel, yet has an enlarged open area 27 designed to serve as a fluid passageway as hereinafter set forth. Shaft portion 22 is integral with the enlarged plunger retainer end 28 which is designed to serve as a retaining means for elastomeric piston 25 as shown in FIG. 3.

Figure 4:
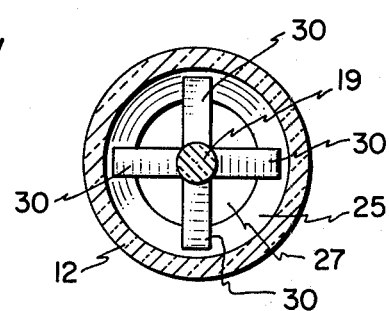
FIG. 4 is an enlarged, transverse, vertical section taken along the line 4—4 in FIG. 3.

A spider portion 29 has a series of arms 30 arranged in quadrature as shown in FIG. 4. These may be molded parts or portions integral with the shaft portion 22. It will be observed that there are many types of equivalent structures which can be used at 30 in FIG. 3, this so as to add support for thrusting against the piston in a direction to the right, see FIG. 2, while at the same time permitting, during such thrusting, the rearward passage of such fluid as may heretofore have been collected in the barrel forwardly of the piston. This is explained hereinafter.

Barrel 12 includes a shouldered aperture 31 which receives a connector element 32. The latter is generally cylinderical in form but may be provided with shoulders at 33 and 34 to accommodate a connector placement stop for connector conduit 35 and also to a facilitate a cemented securement at 31. Conduit 35 serves simply as a drain conduit such that the fluid as is periodically drawn into the barrel of the syringe may be expelled therefrom into a fluid container or some other desired area.

Figure 3:
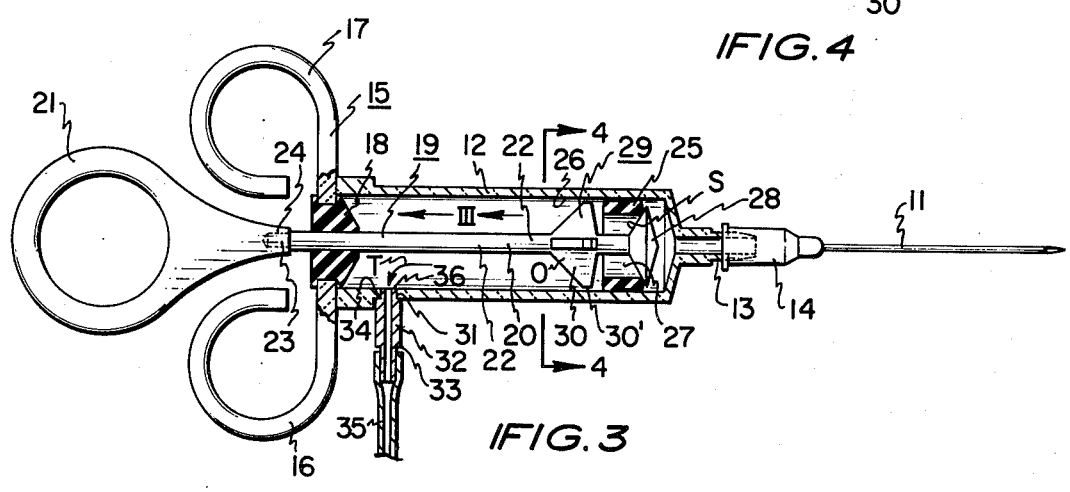
FIG. 3 is similar to FIG. 2 but illustrates the plunger as being thrust to its forward position.

It is noted relative to FIG. 3 that there is ample spacing to provide for clearance on opposite sides of piston 25 relative to plunger retainer end 28 and the series of spider portions 30 comprising a relieved reaction portion 30'. Accordingly, an important feature of the invention relating to the provision of the plunger design, provides for no escape of fluid to the right as the piston 25 is urged to the left as per stroke III in FIG. 3. Thus, the plunger retainer end 28 is sufficient to provide a reaction surface for piston 25 so as to urge the latter in a leftward direction and, thereby, expel or discharge liquid contents within the plunger barrel to the left of retainer end 28 for expression or discharge through connector 32 to conduit 35.

Figure 2:
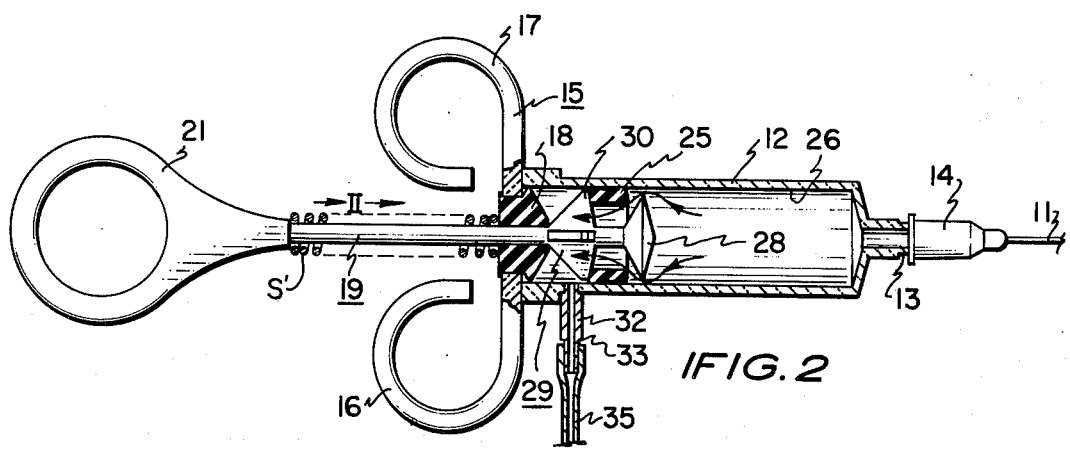
FIG. 2 is a side elevation principally in vertical longitudinal section, taken along the line 2—2 in FIG. 1.

FIG. 2, however, depicts by the developed arcuate arrows within the barrel, the fluid flow that will occur when the plunger is urged home to its retrieved condition relative to the syringe barrel.

It is now possible to discuss the operation of the present syringe. The cannula needle proximate 11 in FIG. 1 is introduced into the patient and the plunger 19 is withdrawn to the left so as to suck in, by virtue of the negative pressure conditions created within the barrel, any fluid as may be in proximity with the cannula. It is noted that the syringe structure is suitable for pumping fluid from the knee or elbow area or, indeed, any of a number of liquid-host areas relating to patients or other subjects.

After the initial withdrawal stroke of the plunger has been completed as per FIG. 1, then the plunger 19 is returned in a direction to the right as shown by the arrow II in FIG. 2, thereby providing for a leakage of fluid that has been collected within the barrel to the right of the plunger, to leak past retainer end 28 and through piston 25 so as to achieve a flow similar to the arrows depiction in FIG. 2. Accordingly, once the plunger has succeeded and advanced completely to the right, so as to reassume the condition shown in FIG. 1, then all of the liquid will have been disposed to the rear of the piston 25, namely, to the left.

At this point in operation the user again retrieves, by thumb ring 21, the plunger 19. This time the plunger retainer end 28 will sealingly engage piston 25 so that there exists a positive action by the forward surface S of retainer end 28, so as to expel fluid in the direction of the arrow T through the connector 32 and conduit 35. It is noted that this expelling of fluid is simultaneously accompanied, see FIG. 3, by the sucking in of a new charge of fluid from a patient. Accordingly, the piston 25 is, in fact, double-acting, serving simultaneously to expel fluid from the rearward area through connector 32 to a sump while also serving to draw in, via suction, liquid in the patient's affected area.

Accordingly, what is presented is a piston construction which by a new design serves as a fluid withdrawing device, such device being provided with structural means for expelling the fluid so withdrawn. Indeed, efficiency of operation is enhanced by the use of a floating piston 25 which is simply alternately sealed to the surface S of retainer end 28. The piston 25 should be made of rubber or other elastomeric material sufficiently resilient to accommodate the slight deformity as shown in FIGS. 2 and 3 as the directional movement of the plunger is reversed. In one form a piston 25 serves to seal the area S of retainer end 28, thereby providing for suction for additional fluid and simultaneously the expression of such fluid outwardly. The spider portion 29, in contrast, serves to retain the piston while providing that the open area of the latter can register with open areas O in the spider configurement so as to provide for a leakage of fluid as shown by the arrows within the barrel in FIG. 2.

The following additional points are to be made:

It is important to note that at no time is the fluid, within the syringe, returned, inadvertently or otherwise, to the patient area, regardless of the direction of movement of the plunger. Secondly, to facilitate ease of operation, the plunger can be spring-biased toward plunger-retraction position, so that solely a manual squeeze is required, i.e., for forward plunger strokes, the spring S' giving an automatic return. See the inventor's U.S. patent application entitled PUMPING-SYRINGE, Ser. No. 505,758 filed Sept. 13, 1974 which is fully incorporated herein by way of reference.

This invention is suitable for a wide variety of fluid viscosities and types of matter bordering on heavy fluids; increased versatility is had as to the latter when the larger bore cannulas ae employed. Where the matter can proceed through the cannula needle, it will proceed through the valving construction of the syringe piston.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

I claim:

1. A pump-type syringe including, in combination, a syringe barrel having a cannula-receiving apertured end, rear finger-retainer means, and a rear closure; a cannula mounted upon said end; a plunger having a shaft sealingly journaled for longitudinal movement in said rear closure and provided with piston means operably disposed within said syringe barrel and so constructed to provide for baffle-type closure during plunger withdrawal strokes and fluid bypass during plunger forward-return strokes, said plunger also having a rearward, enlarged, thumb-depression end; a compression spring operatively interposed between said rear closure and said enlarged thumb-depression end; and drainage port structure provided said barrel rearward of said piston means for all dispositions of the latter.

2. The syringe of claim 1 wherein said piston means comprises a hollow elastomeric piston having squared forward and rear surfaces, said shaft including a plunger retainer end constructed to sealingly engage said piston at said forward surface during return plunger strokes and fluid-bypass piston-support means engaging said piston means at said rear surface on forward plunger strokes; said piston being disposed between said piston-support means and said plunger retainer end, the distance between said piston-support means and said retainer end being greater than the axial dimension of said piston.

3. The structure of claim 2 wherein said fluid-bypass piston support means comprises a spider having a plurality of outwardly extending arms.

4. The structure of claim 1 wherein said piston is uniformty hollow and is constructed to receive said shaft such that a fluid shunting path is provided therebetween.

5. The structure of claim 1 wherein said port structure extends laterally outwardly from said barrel and includes a discharge tube.

* * * * *